(12) United States Patent
Ellman

(10) Patent No.: US 7,862,173 B1
(45) Date of Patent: Jan. 4, 2011

(54) DIGITAL IMAGING OPHTHALMOSCOPE

(75) Inventor: Marc Ellman, El Paso, TX (US)

(73) Assignee: VistaMed, LLC, El Paso, TX (US)

( * ) Notice: Subject to any disclaimer, the term of this patent is extended or adjusted under 35 U.S.C. 154(b) by 0 days.

(21) Appl. No.: 12/511,646

(22) Filed: Jul. 29, 2009

(51) Int. Cl.
  *A61B 3/10* (2006.01)
(52) U.S. Cl. ................................ 351/218; 351/217
(58) Field of Classification Search ............... 351/218, 351/217, 216, 221, 206, 205, 246; 600/112, 600/167, 162
  See application file for complete search history.

(56) References Cited

U.S. PATENT DOCUMENTS

| | | |
|---|---|---|
| D189,554 S | 1/1961 | Armbruster |
| D207,371 S | 4/1967 | Pulos |
| D221,255 S | 7/1971 | Heine |
| D231,949 S | 6/1974 | Pulos |
| D238,100 S | 12/1975 | Pulos |
| 4,208,107 A | 6/1980 | Oharek |
| 4,265,518 A | 5/1981 | Matsumura |
| 4,304,483 A | 12/1981 | Whitten |
| 4,643,546 A | 2/1987 | Richards |
| 4,742,819 A | 5/1988 | George |
| 4,938,584 A | 7/1990 | Suematsu et al. |
| 5,152,295 A | 10/1992 | Kobayashi et al. |
| 5,202,710 A * | 4/1993 | Perkins .................. 351/211 |
| 5,528,323 A | 6/1996 | Fujieda et al. |
| 5,599,276 A | 2/1997 | Hauptli et al. |
| D379,514 S | 5/1997 | Laun et al. |
| 5,646,709 A * | 7/1997 | Carter .................... 351/218 |
| 5,658,235 A | 8/1997 | Priest et al. |
| 5,793,468 A | 8/1998 | Shalon et al. |
| 5,861,939 A | 1/1999 | Heacock |
| 5,885,214 A | 3/1999 | Monroe et al. |
| 5,892,568 A * | 4/1999 | Carter .................... 351/218 |
| D426,920 S | 6/2000 | Georgescu |

(Continued)

FOREIGN PATENT DOCUMENTS

WO  WO/2006/086269  8/2006

OTHER PUBLICATIONS

James Tyrrell, "Ophthalmoscope Goes Digital", optics.org (Jul. 30, 2004) http://optics.org/cws/article/research/19973.

(Continued)

*Primary Examiner*—Hung X Dang
(74) *Attorney, Agent, or Firm*—Adam R. Stephenson, Ltd.

(57) ABSTRACT

An opthalmoscope. Implementations include a handle coupled to a head where the head includes a front section coupled with a diopter wheel and the front section includes a view window. A back section fixedly attached to the front section includes a diopter number viewer, a trigger button, and a digital imaging section. The digital imaging section may include a liquid crystal display (LCD) screen. The trigger button may be adjacent to the handle and may be positioned opposite the front section between the handle and the LCD screen. The back section may include a rounded projection rotatably coupled with a central hole in the diopter wheel extending from a diopter surface substantially parallel with and in close proximity to the diopter wheel. The diopter number viewer may extend from the diopter surface away from the diopter wheel and may include an opening configured to expose a diopter number.

13 Claims, 6 Drawing Sheets

U.S. PATENT DOCUMENTS

| | | | |
|---|---|---|---|
| 6,112,114 A | 8/2000 | Dreher | |
| D441,076 S | 4/2001 | Cooper et al. | |
| 6,275,718 B1 | 8/2001 | Lempert | |
| 6,319,199 B1 | 11/2001 | Sheehan et al. | |
| 6,432,046 B1 | 8/2002 | Yarush et al. | |
| 6,511,420 B1 | 1/2003 | Farrell et al. | |
| 6,554,765 B1 | 4/2003 | Yarush et al. | |
| 6,743,168 B2 | 6/2004 | Luloh et al. | |
| 6,761,561 B2 | 7/2004 | Mandelkern et al. | |
| 6,850,631 B1 | 2/2005 | Oda et al. | |
| 6,862,036 B2 | 3/2005 | Adair et al. | |
| 7,086,859 B2 | 8/2006 | Gregorio et al. | |
| 7,211,042 B2 | 5/2007 | Chatenever et al. | |
| 7,237,896 B2 | 7/2007 | Silverbrook et al. | |
| D550,842 S | 9/2007 | Koch et al. | |
| 7,284,863 B2 | 10/2007 | Kay-Wilson | |
| 7,290,882 B2 | 11/2007 | Collins et al. | |
| 7,364,297 B2 | 4/2008 | Goldfain et al. | |
| 7,537,340 B2 | 5/2009 | Yamaguchi et al. | |
| 7,542,628 B2 | 6/2009 | Lolacono et al. | |
| 7,604,351 B2 | 10/2009 | Fukuma et al. | |
| 7,657,127 B2 | 2/2010 | Lolacono et al. | |
| 7,750,579 B2 | 7/2010 | Aiello | |
| 2004/0183482 A1 | 9/2004 | Roberts et al. | |
| 2005/0110949 A1 | 5/2005 | Goldfain et al. | |
| 2005/0171399 A1 | 8/2005 | Rich et al. | |
| 2007/0106117 A1 | 5/2007 | Yokota | |
| 2008/0002152 A1 | 1/2008 | Collins et al. | |
| 2008/0143840 A1 | 6/2008 | Corkum et al. | |

OTHER PUBLICATIONS

"AMD-2020 Direct Ophthalmoscope", AMD Global Telemedicine, available at http://www.amdtelemedicine.com/telemedicine-equipment/ophthalmology/amd-2020-direct-ophthalmoscope.html, last visted May 26, 2010.

* cited by examiner

DIGITAL IMAGING OPHTHALMOSCOPE

BACKGROUND

1. Technical Field

Aspects of this document relate generally to imaging devices, such as opthalmoscopes.

2. Background Art

Conventionally, opthalmoscopes are used to observe the rear of the eye, particularly the structures of the retina. A discussion of conventional opthalmoscope components, structure, and uses may be found in U.S. Pat. No. 3,948,585 to Heine, et al., entitled "Opthalmoscope Examination Pattern Having Slit and Surrounding Ring," issued Apr. 6, 1976, the disclosure of which is hereby incorporated entirely herein by reference.

SUMMARY

Implementations of digital imaging opthalmoscopes like those disclosed in this document may include a handle coupled to a head where the head includes a front section coupled with a diopter wheel and the front section includes a view window. A back section fixedly attached to the front section may also be included where the back section includes a diopter number viewer, a trigger button, and a digital imaging section. The digital imaging section may include a liquid crystal display (LCD) screen and may be adapted to display an object in the field of view of the view window on the LCD screen. The trigger button may be adjacent to the handle and may be positioned opposite the front section between the handle and the LCD screen. The back section may include a rounded projection rotatably coupled with a central hole in the diopter wheel where the rounded projection extends from a diopter surface in the back section substantially parallel with and in close proximity to the diopter wheel. The diopter number viewer may extend from the diopter surface away from the diopter wheel and may include an opening configured to expose a diopter number on the diopter wheel.

Implementations of opthalmoscopes may include one, all, or any of the following:

The diopter number may permit light from a light source included in the handle to illuminate the diopter number.

The digital imaging section may be configured to digitally zoom the image of the object displayed on the LCD screen.

The digital imaging section may be configured to store one or more images of the object in the field of view of the view window in memory associated with the digital imaging section when the trigger button is pressed.

The digital imaging section may be configured to allow annotations to be captured and stored in the memory for the one or more stored images of the object.

The digital imaging section may further include one or more image review buttons, a Universal Serial Bus (USB) port, and an external switch.

Implementations of a head for a digital imaging opthalmoscope may include a front section having a view window and fixedly attached to a back section. The front section and back section may include an image axis where the view window of the front section lies on the image axis and the back section further includes a diopter wheel including a plurality of diopters. Each diopter may be configured to align with the image axis through rotation of the diopter wheel. A doublet lens may be included and located on the image axis and configured to focus an image of an object in the field of view of the view window on a photosensor located on the image axis which is included in a digital imaging section included in the back section. A rounded projection may be included which is rotatably coupled with a central hole in the diopter wheel where the rounded projection extends from a diopter surface in the back section substantially parallel with and in close proximity to the diopter wheel. A diopter number viewer may be included that extends from the diopter surface away from the diopter wheel and includes an opening configured to expose a diopter number on the diopter wheel. The digital imaging section may be configured to use the photosensor to create a digital image of the object and to display the digital image on a liquid crystal display (LCD) screen included in the digital imaging section and to store one or more images of the object in memory associated with the digital imaging section when a trigger button located adjacent to the diopter number viewer is pressed.

Implementations of a head for a digital imaging opthalmoscope may include one, all, or any of the following:

The diopter number viewer may permit light from a light source included in the handle to illuminate the diopter number.

The digital imaging section may be configured to digitally zoom the image of the object displayed on the LCD screen.

The digital imaging section may further include one or more image review buttons, a Universal Serial Bus (USB) port, and an external switch.

A portion of the viewing axis between the plurality of diopters and the doublet lens may be a nearly infinite corrected path.

The digital imaging section may be configured to allow annotations to be captured and stored in the memory for the one or more stored images of the object.

In an opthalmoscope with a handle and a front section including a view window, an improvement may include a back section fixedly attached to the front section where the back section includes a digital imaging section. The digital imaging section may include a liquid crystal display (LCD) screen and may be adapted to display an object in the field of view of the view window on the LCD screen. The digital imaging section may include one or more imaging review buttons and a Universal Serial Bus (USB) port. A trigger button may be included adjacent to the handle and positioned opposite the front section between the handle and the LCD screen. A diopter number viewer may extend away from a diopter wheel located between the front section and the back section and may extend from a diopter surface included in the back section where the diopter surface is substantially parallel with and in close proximity to the diopter wheel. The diopter number viewer may include an opening configured to expose a diopter number on the diopter wheel and the diopter number viewer may be configured to permit light emitted from the handle to illuminate the diopter number.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components or assembly procedures disclosed herein. Many additional components and assembly procedures known in the art consistent with the intended digital imaging opthalmoscope and/or assembly procedures for a digital imaging opthalmoscope will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such digital imaging opthalmoscopes and implementing components, consistent with the intended operation.

Figure 1:
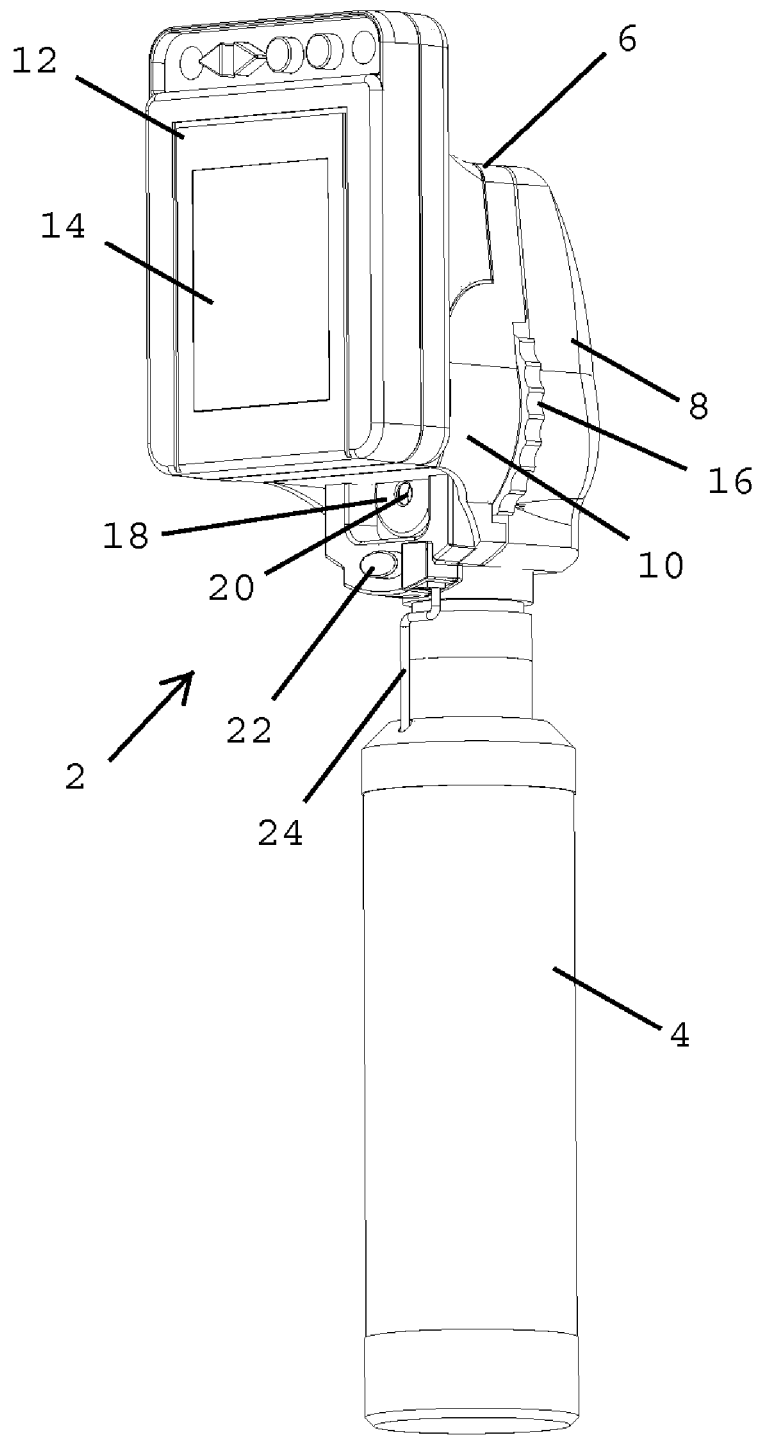
FIG. 1 is a rear perspective view of an implementation of an opthalmoscope.

Referring to FIG. 1, an implementation of a digital imaging opthalmoscope (hereinafter "opthalmoscope") 2 is illustrated. The opthalmoscope 2 shown in FIG. 1 is a direct opthalmoscope; however, other opthalmoscope types and sizes, such as indirect types or miniature opthalmoscopes, may also utilize the principles disclosed in this document. In addition, the principles disclosed in this document could be applied to other endoscope types, such as otoscopes and laryngoscopes. The opthalmoscope 2 includes a handle 4 that includes a light source and may in various implementations contain various apertures selectable by a user with an aperture wheel. Any of a wide variety of conventional opthalmoscope handle designs utilizing various light sources and related structures may be employed, such as, by non-limiting example, incandescent light sources, halogen light sources, and any other source of light. In particular implementations, a light emitting diode (LED) light source may be utilized, which may be pulsed. The opthalmoscope 2 also includes a head 6 that has a front section 8 fixedly attached to a back section 10. As used in this document, "fixedly attached" means coupled using any type of fastener, such as, by non-limiting example, a screw, pin, glue, or other structure that joins two pieces.

As illustrated in FIG. 1, the back section 10 includes a digital imaging section 12 that includes a liquid crystal display (LCD) screen 14. The digital imaging section 12 and the LCD screen 14 are adapted to display images of objects (such as the interior structure of a patient's eye) that are in the field of view of the opthalmoscope 2. A diopter wheel 16 is also included that in particular implementations may be part of the back section 10 and in other implementations may be considered to be located between the back section 10 and the front section 8. The diopter wheel 16 rotates within the opthalmoscope 2 and contains a plurality of diopters, which are corrective and/or magnifying lenses that adjust the image being viewed by the opthalmoscope 2. Each of the diopters may have a specific number associated with it included on the diopter wheel 16, and that number is visible through a diopter number viewer 18 included in the back section 10. As illustrated, the diopter number viewer 18 includes a hole 20 through which the particular number of the diopter being used is made visible. In particular implementations, light from the handle may be directed into the diopter number viewer 18 to illuminate the diopter number on the diopter wheel 16 and enable it to be visible through hole 20.

The back section 10 also includes a trigger switch 22 located adjacent to the handle 4 and opposite the front section 8. The trigger switch 22 is also adjacent to the diopter number viewer 18. A wire 24 may be included in particular implementations of opthalmoscopes 2 to carry power from the handle 4 to the digital imaging section 12. In some implementations, the wire 24 may be routed outside the handle 4 as shown. In other implementations, the wire 24 may be routed internally within the handle 4 and head 6. In particular implementations, the routing may take place through use of a coupling adapter between the handle and the head. In some implementations, backup or primary power sources may be directly included in the digital imaging section 12 itself, such as through the use of batteries or other stored power sources.

Figure 2:
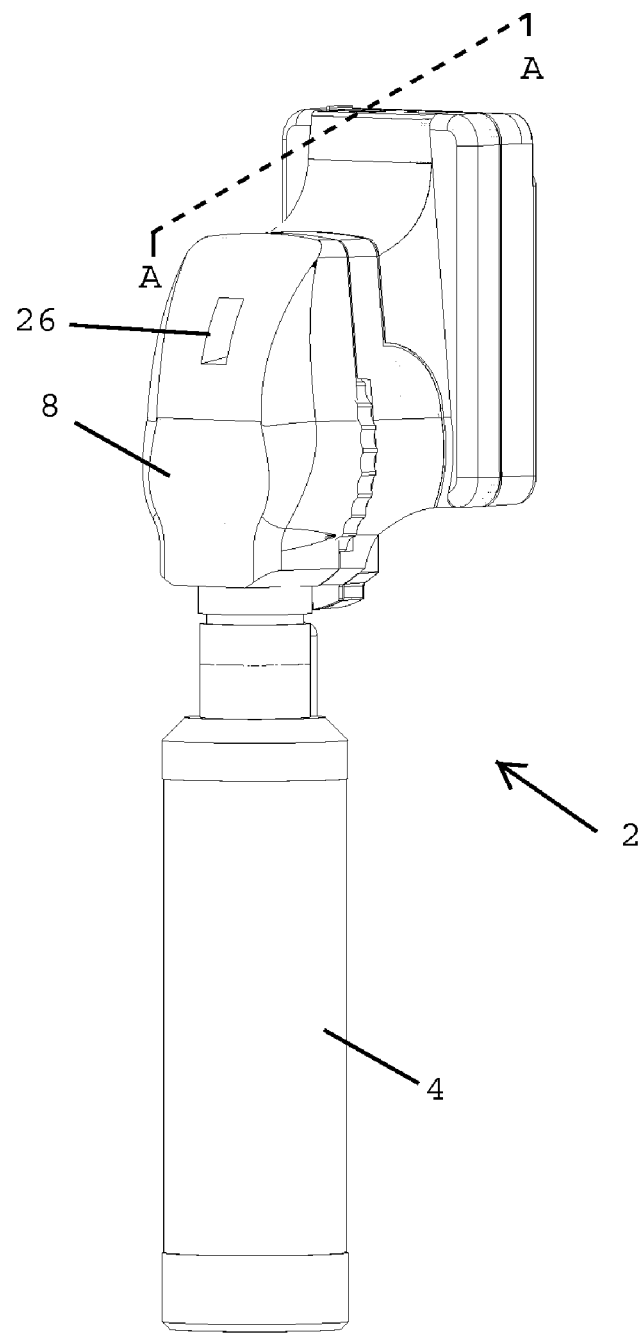
FIG. 2 is a front perspective view of an implementation of an opthalmoscope showing sectional line A.

Referring to FIG. 2, a front perspective view of the opthalmoscope 2 of FIG. 1 is illustrated, showing the sectional line A. As shown, the front section 8 includes a view window 26 that allows light from the handle 4 to exit the opthalmoscope 2 and reflected light from the object being viewed (such as the retina of a patient) to enter, provided the object is in the field of view of the view window 26. Also as illustrated, the front section 8 and handle 4 for particular implementations of opthalmoscopes 2 may be assembled from a conventional opthalmoscope 2, such as one manufactured by Welch Allyn Corporation of Skaneateles Falls, N.Y. In other implementations, the opthalmoscope 2 may be constructed using all new parts.

Figure 3:
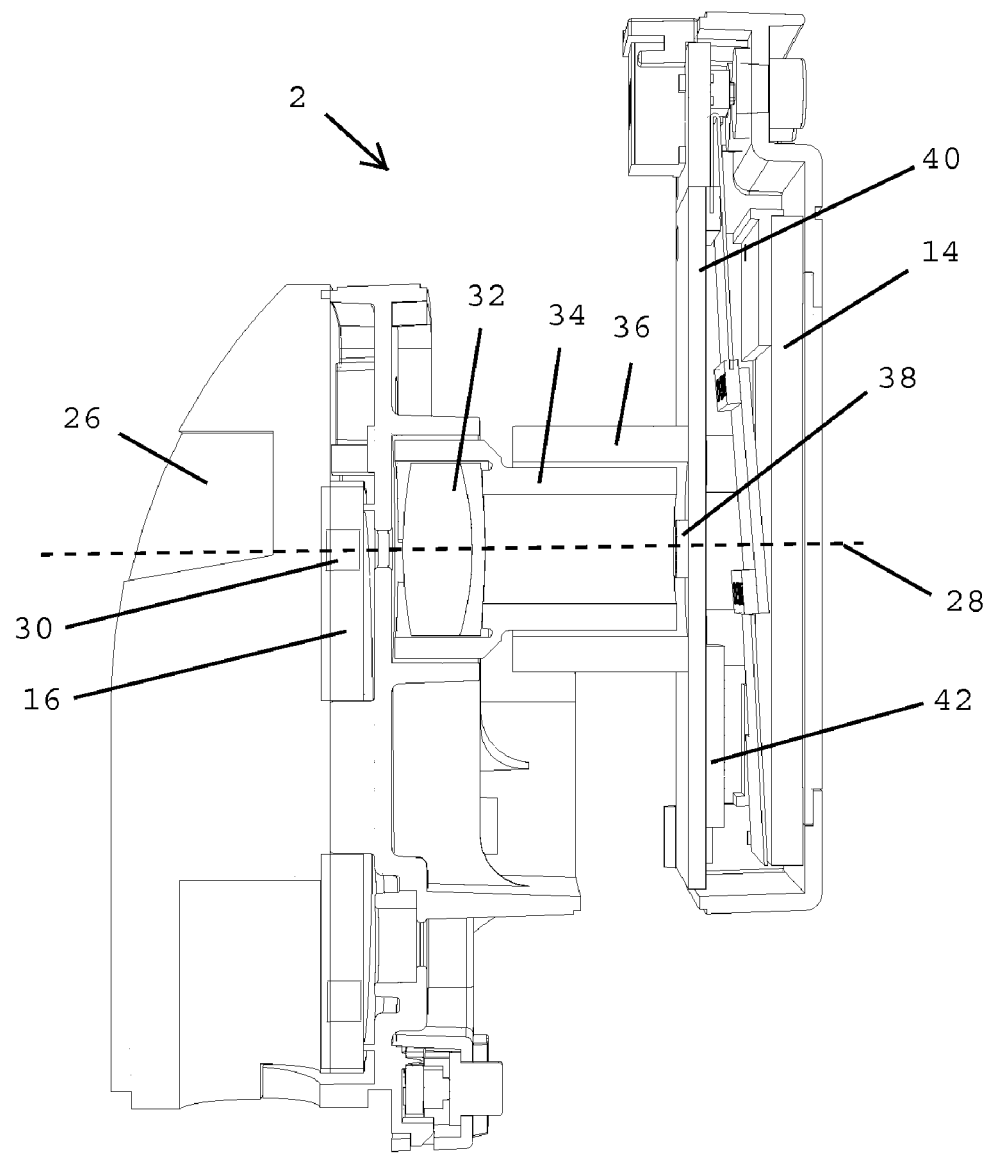
FIG. 3 is a cross sectional view taken along sectional line A in FIG. 2 with portions of structure removed for clarity.

Referring to FIG. 3, a cross sectional view along sectional line A of the implementation of an opthalmoscope 2 illustrated in FIGS. 1 and 2 is illustrated. Some of the components (such as the cover over the digital imaging section 12) have been removed from the cross section to enable better visibility of particular components. As illustrated, a viewing axis 28 may exist within the opthalmoscope 2. Light from the view window 26 may pass through one of the plurality of diopters 30 in the diopter wheel 16. The light may then pass through a doublet lens 32 supported within a lens tube 34 and secured by a lens holder 36. The doublet lens 32 focuses the light on a photosensor 38 that converts the light to a digital image. The photosensor 38 is associated with one or more circuit boards 40 and memory 42 which receive the digital image and process it using one or more processors so that it can be displayed on the LCD screen 14. In the implementation illustrated in FIG. 3, the optical configuration of the doublet lens 32, the lens tube 34, and the photosensor 38 may create a nearly infinite corrected path along the portion of the viewing axis between the doublet lens 32 and the plurality of diopters 30. By nearly infinite corrected path is meant an optical path of about 20 meters, which, given the size of the plurality of diopters 30, is a very large separation distance. Accordingly, in particular implementations, the actual distance between the plurality of diopters 30 and the doublet lens 32 is not critical, and can be closer or substantially infinitely far away while retaining the ability to focus the image being received at the view window 26.

A wide variety of components may be utilized in various implementations of opthalmoscopes 2. For example, while a doublet lens is utilized in the implementation illustrated in FIG. 3, a single lens or other combination of lenses could be used. For the exemplary purposes of this disclosure, the photosensor may be a Video Graphics Array (VGA) image sensor manufactured by Omnivision Technologies, Inc. of Santa Clara, Calif. The LCD screen may be a screen manufactured by Displaytech, Ltd., of ChangAn, GuangDong, China distributed by SEAComp, Inc. of Carlsbad, Calif. A wide variety of other components may be included in implementations of digital imaging sections 12.

Figure 4:
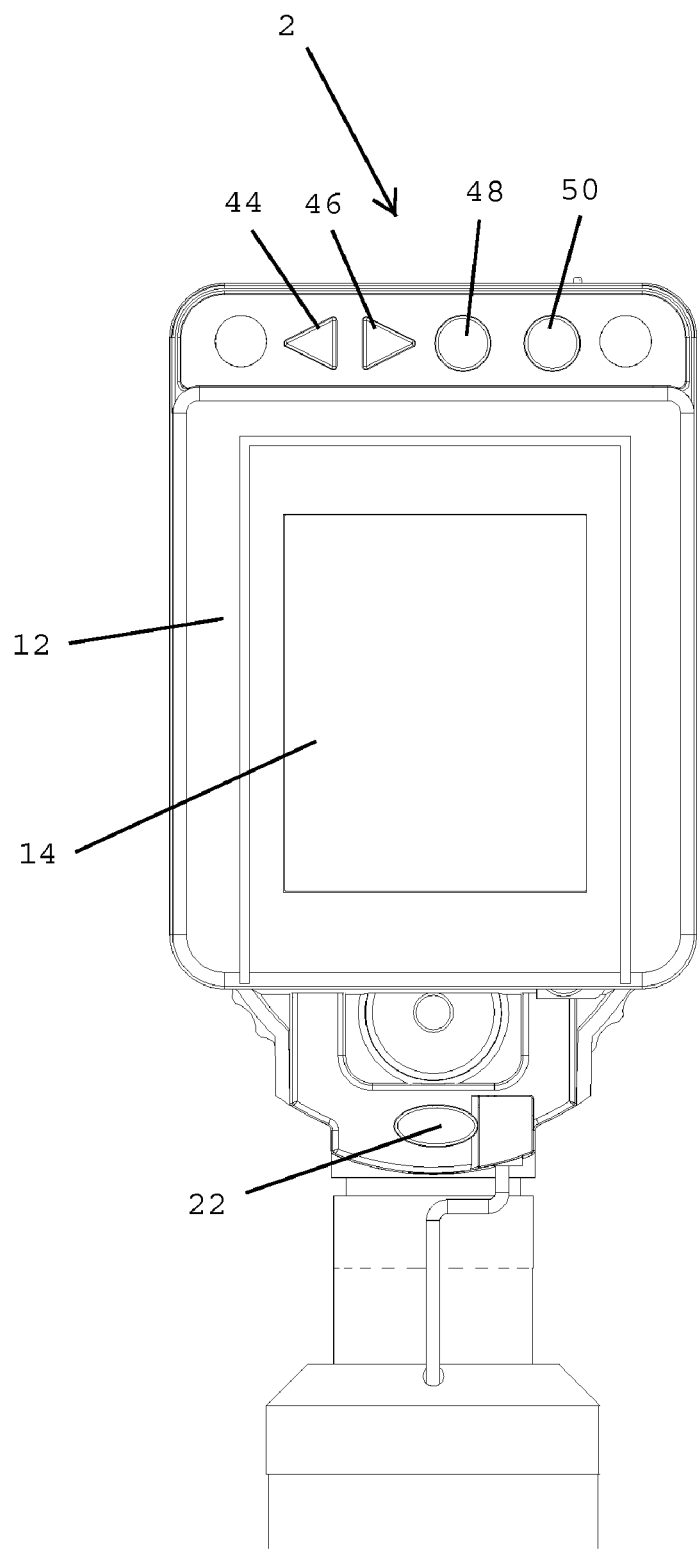
FIG. 4 is a rear detail view of an implementation of an opthalmoscope showing an implementation of a digital imaging section.

Referring to FIG. 4, a rear detail view of an opthalmoscope 2 is illustrated. Around and/or adjacent to the LCD screen 14, a plurality of image review buttons 44, 46, 48, 50 are located. Each of the image review buttons 44, 46, 48, 50 may perform a single or multiple functions. For example, the image review buttons 44, 46 may allow a user to select which of a plurality of stored images will be displayed on the LCD screen 14. Either or both of image review buttons 48 or 50 may implement a digital zoom function within the digital imaging section 12 that allows the image displayed on the LCD screen 14 to be magnified digitally using any of a wide variety of conventional methods without requiring any optical movement. The plurality of image review buttons 44, 46, 48, and 50 may enable many other desired functions and capabilities of the digital imaging section 12 such as, by non-limiting example, adding marks to the image(s) to identify the image as being from the right or left eye, changing brightness, changing contrast, changing date stamps visible on the image, adding text to the image, or any other desired image adjustment, annotation, or optimization function. Among these may be enabling the capturing and storing of annotations made to an image displayed on the LCD screen 14. The annotations may be handwritten or placed by a user's hand and may be entered using a stylus, finger, or any other man-machine interaction interface. Any of a wide variety of systems and methods for capturing and storing the annotations may be utilized in particular implementations, such as those disclosed in U.S. Pat. No. 5,637,871 to Piety et al., entitled "Portable Digital Infrared Thermography System," issued Jun. 10, 1997 or U.S. Patent Application Publication No. 20020051262 to Nuttall et al., entitled "Image Capture Device with Handwritten Annotation," published May 2, 2002, the disclosures of which are hereby incorporated entirely herein by reference. In implementations of opthalmoscopes 2 utilizing annotating of images, the LCD screen 14 may also include touch sensing capabilities or utilize other stylus tracking systems and/or methods. The annotations may be stored as part of the images in memory or may be stored separately from the images in memory.

Implementations of trigger buttons 22 may be utilized in combination with implementations of digital imaging sections 12 to enable recording of live and/or static images being displayed on the LCD screen 14. To accomplish this, a user may ensure that a desired image is being displayed on the LCD screen 14 and then press the trigger button 22. Various messages may be displayed on the LCD screen 14 regarding whether the user desires to save the image or not and the image review buttons 44, 46, 48, and 50 may be also be involved in the specific steps of storing the image. The images may be stored to the memory 42 internal to the digital imaging section 12 and/or they may be saved to an external storage device. In particular implementations, a Universal Serial Bus (USB) port may be included in a surface of the digital imaging section 12 which may allow transfer and/or storage of images to a storage device such as a memory stick, external hard drive or other desired storage device or transfer of live video to another display or storage device. In particular implementations, the digital imaging section 12 may include an external switch that may perform a variety of functions including, by non-limiting example, turning off the LCD screen, adjusting the brightness of the LCD screen, changing a mode of operation of the digital imaging section 12, or any other desired function. A wide variety of other input/output connector types may also be included in particular implementations, such as, by non-limiting example, FireWire®, Red Green Blue (RGB) outputs, Recommended Standard (RS)-232 serial interfaces, wireless interfaces, Bluetooth® interfaces, or any other wired or wireless interface adapted to transmit data from the digital imaging section to another device.

Figure 5:
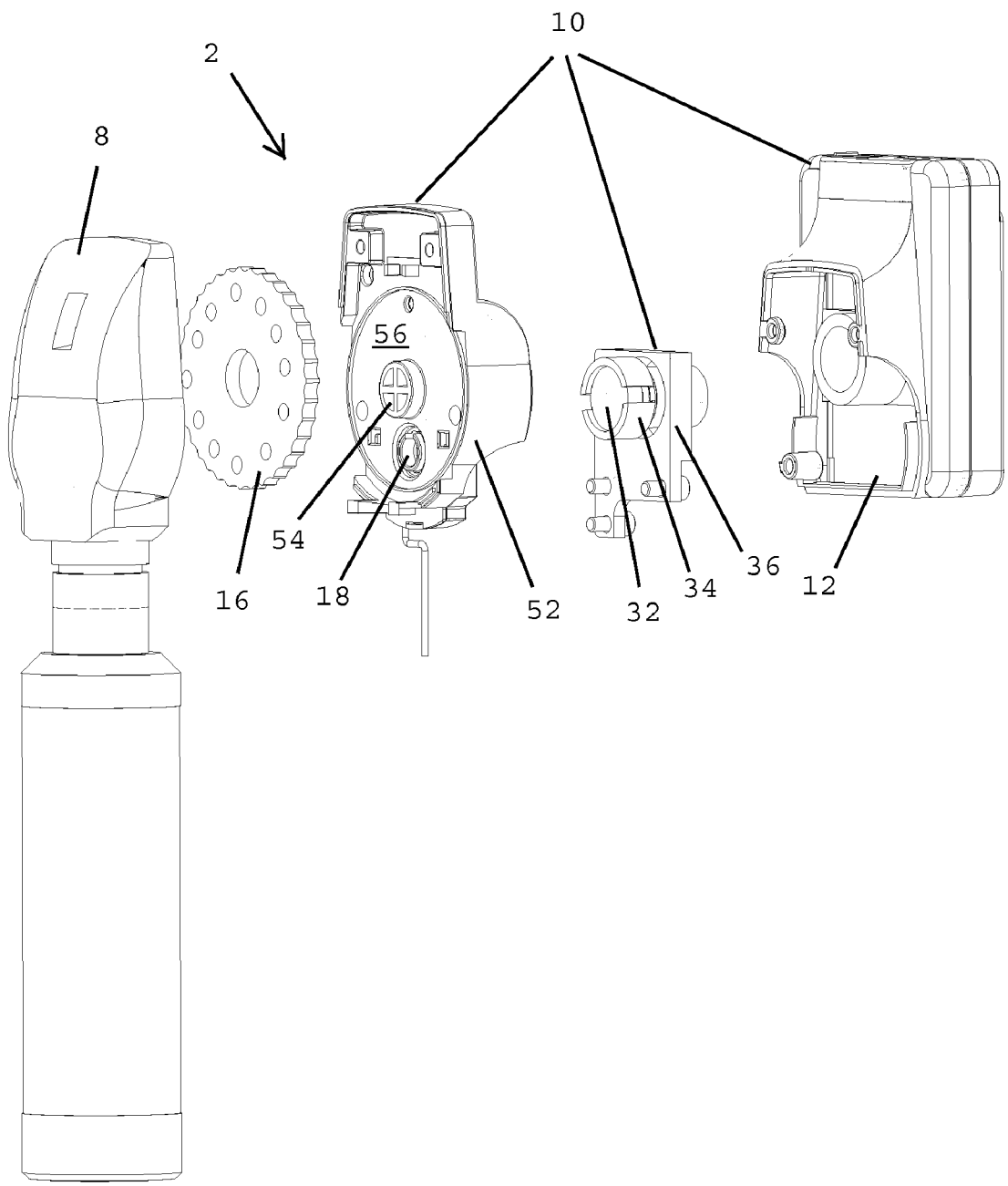
FIG. 5 is a partially exploded front view of an implementation of an opthalmoscope.
Figure 6:
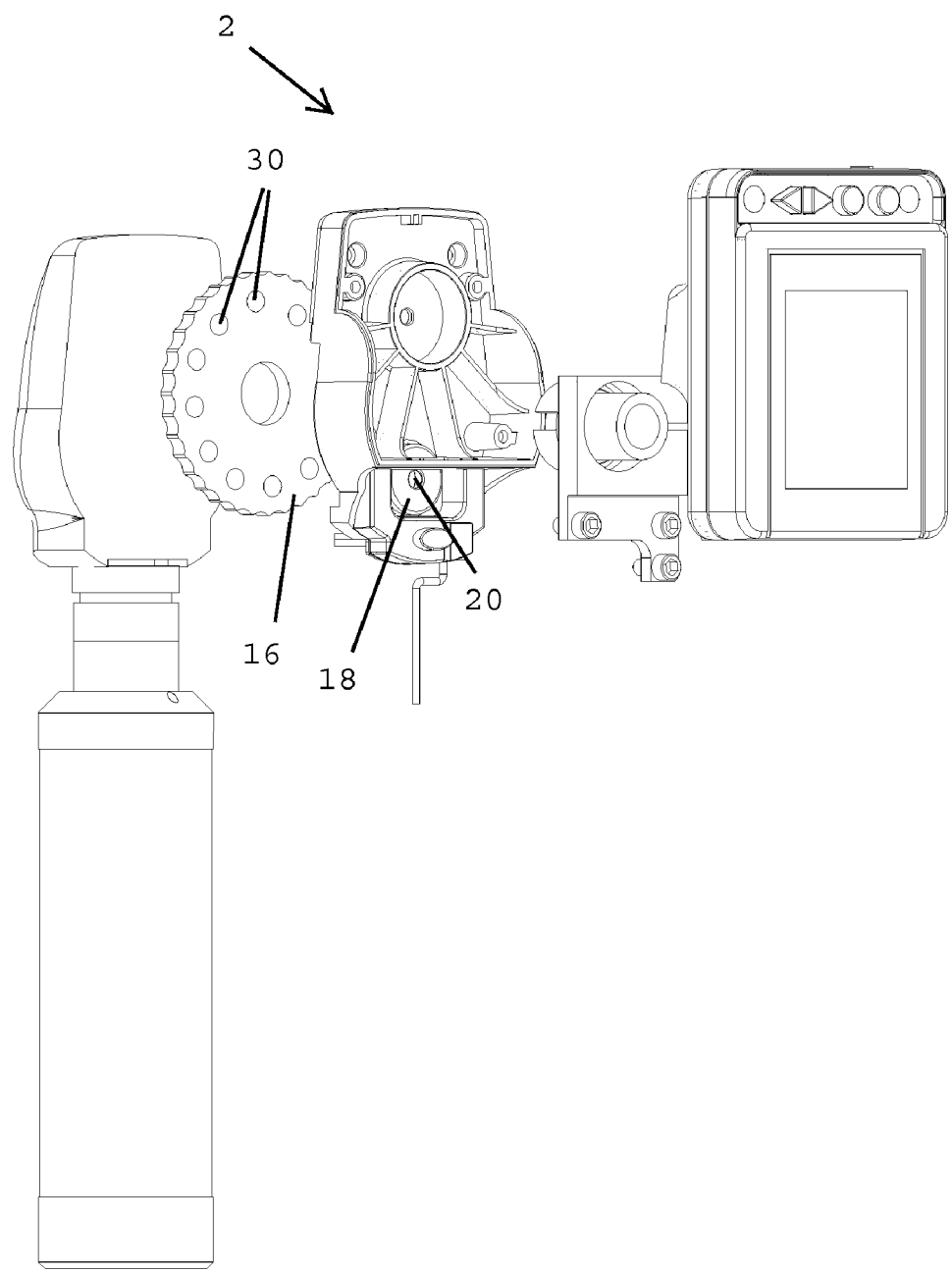
FIG. 6 is a partially exploded rear view of an implementation of an opthalmoscope.

Referring to FIG. 5, a partially exploded front view of the implementation of an opthalmoscope 2 of FIGS. 1 and 2 is illustrated. As illustrated, the exploded portions are those of the back section 10 showing the digital imaging section 12, the doublet lens 32/lens tube 34/lens holder 36 assembly, and a portion 52 of the back section 10 that fixedly attaches to the front section 8. As illustrated, the portion 52 of the back section 10 includes a rounded projection 54 that extends from a diopter surface 56 that is substantially parallel to the diopter wheel 16 and is close proximity to the diopter surface 56 when the opthalmoscope 2 is assembled. The rounded projection 54 rotatably couples with a central hole 58 in the diopter 16. As illustrated, the diopter number viewer 18 extends from the diopter surface 56 away from the diopter wheel 16, which makes it appear raised from the surface of the portion 52 of the back section 10 when viewed from the rear, as is illustrated in FIG. 6. Also illustrated in the partially exploded rear view of the opthalmoscope 2 of FIG. 6 is the position of the hole 20 that allows viewing of diopter numbers (not shown) associated with the plurality of diopters 30 on the diopter wheel 16 during operation.

Implementations of LCD screens like those disclosed in this document may be directly attached to the head or digital imaging section, or may be fixedly attached through use of a hinge that allows the LCD screen to be moved in any desired orientation relative to the head. In implementations where the LCD screen can be moved using a hinge, a viewfinder may be exposed when the LCD screen is moved that allows a user of the opthalmoscope to use his or her eye directly, and then utilize the trigger button or other buttons to save an image of what is being viewed. In particular implementations, this may take place by splitting the image and sending a copy to the LCD screen and a copy to the user's eye; in other implementations, splitting of the image may not be used. In some implementations, image display may take place using a separate wired or wirelessly connected device, and images and/or real time video of what is being observed may be made available for viewing on external displays, such as a projector, television, or computer display. Such implementations may be useful in teaching situations to enable the students to see what the user of the opthalmoscope is viewing simultaneously. In other implementations, a viewfinder may be included that allows a user to use his or her eye directly without requiring movement/adjustment of the LCD screen.

In places where the description above refers to particular implementations of digital imaging opthalmoscopes, it should be readily apparent that a number of modifications may be made without departing from the spirit thereof and that these implementations may be applied to other digital imaging opthalmoscope implementations.

The invention claimed is:
1. An opthalmoscope comprising:
a handle coupled to a head, wherein the head comprises:
  a front section coupled with a diopter wheel, the front section including a view window; and
  a back section fixedly attached to the front section, the back section comprising a diopter number viewer, a trigger button, and a digital imaging section, the digital imaging section comprising a liquid crystal display (LCD) screen and adapted to display an object in a field of view of the view window on the LCD screen;

wherein the trigger button is adjacent to the handle and positioned opposite the front section between the handle and the LCD screen; and wherein the back section comprises a rounded projection rotatably coupled with a central hole in the diopter wheel, the rounded projection extending from a diopter surface in the back section substantially parallel with and in close proximity to the diopter wheel; and wherein the diopter number viewer extends from the diopter surface away from the diopter wheel and comprises an opening configured to expose a diopter number on the diopter wheel.

2. The opthalmoscope of claim 1, wherein the diopter number viewer permits light from a light source included in the handle to illuminate the diopter number.

3. The opthalmoscope of claim 1, wherein the digital imaging section is configured to digitally zoom an image of the object displayed on the LCD screen.

4. The opthalmoscope of claim 1, wherein the digital imaging section is configured to store one or more images of the object in the field of view of the view window in memory associated with the digital imaging section when the trigger button is pressed.

5. The opthalmoscope of claim 4, wherein the digital imaging section is configured to allow annotations to be captured and stored in the memory for the one or more stored images of the object.

6. The opthalmoscope of claim 1, wherein the digital imaging section further comprises one or more image review buttons, a Universal Serial Bus (USB) port, and an external switch.

7. A head for an opthalmoscope comprising:
a front section including a view window and fixedly attached to a back section, the front section and back section comprising a viewing axis where the view window of the front section lies on the viewing axis and the back section further comprises:
a diopter wheel comprising a plurality of diopters, each diopter being configured to align with the viewing axis through rotation of the diopter wheel;
a doublet lens located on the viewing axis, the doublet lens being configured to focus an image of an object in a field of view of the view window on a photosensor located on the viewing axis and included in a digital imaging section comprised in the back section;
a rounded projection rotatably coupled with a central hole in the diopter wheel, the rounded projection extending from a diopter surface in the back section substantially parallel with and in close proximity to the diopter wheel; and
a diopter number viewer extending from the diopter surface away from the diopter wheel and including an opening configured to expose a diopter number on the diopter wheel;
wherein the digital imaging section is configured to use the photosensor to create a digital image of the object and to display the digital image on a liquid crystal display (LCD) screen included in the digital imaging section and to store one or more images of the object in memory associated with the digital imaging section when a trigger button located adjacent to the diopter number viewer is pressed.

8. The head of claim 7, wherein the diopter number viewer permits light from a light source included in the handle to illuminate the diopter number.

9. The head of claim 7, wherein the digital imaging section is configured to digitally zoom the digital image of the object displayed on the LCD screen.

10. The head of claim 7, wherein the digital imaging section further comprises one or more image review buttons, a Universal Serial Bus (USB) port, and an external switch.

11. The head of claim 7, wherein a portion of the viewing axis between the plurality of diopters and the doublet lens is a nearly infinite corrected path.

12. The head of claim 7, wherein the digital imaging section is configured to allow annotations to be captured and stored in the memory for the one or more stored images of the object.

13. In an opthalmoscope having a handle and a front section with a view window, the improvement comprises:
a back section fixedly attached to the front section, the back section comprising:
a digital imaging section, the digital imaging section comprising a liquid crystal display (LCD) screen and adapted to display an object in a field of view of the view window on the LCD screen, the digital imaging section including one or more image review buttons and a Universal Serial Bus (USB) port;
a trigger button adjacent to the handle and positioned opposite the front section between the handle and the LCD screen; and
a diopter number viewer extending away from a diopter wheel located between the front section and the back section, the diopter number viewer extending from a diopter surface included in the back section where the diopter surface is substantially parallel with and in close proximity to the diopter wheel;
wherein the diopter number viewer comprises an opening configured to expose a diopter number on the diopter wheel and the diopter number viewer is configured to permit light emitted from the handle to illuminate the diopter number.

* * * * *